United States Patent
Otis et al.

(10) Patent No.: US 9,737,248 B1
(45) Date of Patent: *Aug. 22, 2017

(54) CANCELLATION OF A BASELINE CURRENT SIGNAL VIA CURRENT SUBTRACTION WITHIN A LINEAR RELAXATION OSCILLATOR-BASED CURRENT-TO-FREQUENCY CONVERTER CIRCUIT

(71) Applicant: Verily Life Sciences LLC, Mountain View, CA (US)

(72) Inventors: Brian Otis, Sunnyvale, CA (US); Nathan Pletcher, Mountain View, CA (US)

(73) Assignee: Verily Life Sciences LLC, Mountain View, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/190,358

(22) Filed: Jun. 23, 2016

Related U.S. Application Data

(63) Continuation of application No. 13/610,788, filed on Sep. 11, 2012, now Pat. No. 9,398,868.

(51) Int. Cl.
| | |
|---|---|
| *A61B 5/00* | (2006.01) |
| *A61B 5/1477* | (2006.01) |
| *H03K 4/502* | (2006.01) |
| *H03K 3/037* | (2006.01) |
| *A61B 5/145* | (2006.01) |
| *H04B 1/40* | (2015.01) |

(52) U.S. Cl.
CPC ............ *A61B 5/1477* (2013.01); *A61B 5/002* (2013.01); *A61B 5/0004* (2013.01);
(Continued)

(58) Field of Classification Search
None
See application file for complete search history.

(56) References Cited

U.S. PATENT DOCUMENTS 3,614,306 A * 10/1971 Goldberg ........... H04N 1/00567
358/304
3,958,560 A 5/1976 March
(Continued)

FOREIGN PATENT DOCUMENTS

| | | |
|---|---|---|
| EP | 0369942 | 5/1990 |
| EP | 0686372 | 12/1995 |

(Continued)

OTHER PUBLICATIONS

Adler, "What types of statistical analysis do scientists use most often?" O'Reilly Community, Jan. 15, 2010, 2 pages, http://broadcast.oreilly.com/2010/01/what-types-of-statistical-anal.html, Last accessed Sep. 4, 2012.

(Continued)

*Primary Examiner* — Jacqueline Cheng
*Assistant Examiner* — Michael R Bloch
(74) *Attorney, Agent, or Firm* — McDonnell Boehnen Hubert & Berghoff LLP

(57) ABSTRACT

This disclosure relates to systems and/or methods for subtracting in the current domain an output current primary signal from a primary sensor from an output current reference signal from a reference sensor to produce a frequency output signal indicative of the difference between the output current primary signal and the output current reference signal.

12 Claims, 9 Drawing Sheets

(52) U.S. Cl.
CPC ........ *A61B 5/0022* (2013.01); *A61B 5/14507* (2013.01); *A61B 5/14532* (2013.01); *A61B 5/6821* (2013.01); *A61B 5/742* (2013.01); *H03K 3/0377* (2013.01); *H03K 4/502* (2013.01); *H04B 1/40* (2013.01)

(56) References Cited

U.S. PATENT DOCUMENTS

| | | |
|---|---|---|
| 4,014,321 A | 3/1977 | March |
| 4,055,378 A | 10/1977 | Feneberg et al. |
| 4,122,942 A | 10/1978 | Wolfson |
| 4,136,250 A | 1/1979 | Mueller et al. |
| 4,143,949 A | 3/1979 | Chen |
| 4,153,641 A | 5/1979 | Deichert et al. |
| 4,214,014 A | 7/1980 | Hofer et al. |
| 4,226,245 A * | 10/1980 | Bennett, Jr. ............ G01R 29/02 607/27 |
| 4,277,975 A * | 7/1981 | Pinkham ................ G01K 7/245 374/1 |
| 4,309,085 A | 1/1982 | Morrison |
| 4,312,575 A | 1/1982 | Peyman et al. |
| 4,401,371 A | 8/1983 | Neefe |
| 4,463,149 A | 7/1984 | Ellis |
| 4,555,372 A | 11/1985 | Kunzler et al. |
| 4,604,479 A | 8/1986 | Ellis |
| 4,632,844 A | 12/1986 | Yanagihara et al. |
| 4,686,267 A | 8/1987 | Ellis et al. |
| 4,740,533 A | 4/1988 | Su et al. |
| 4,826,936 A | 5/1989 | Ellis |
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,135,297 A | 8/1992 | Valint et al. |
| 5,162,984 A * | 11/1992 | Castagnet ............ H02M 7/155 363/143 |
| 5,177,165 A | 1/1993 | Valint et al. |
| 5,177,168 A | 1/1993 | Baron et al. |
| 5,219,965 A | 6/1993 | Valint et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,358,995 A | 10/1994 | Lai et al. |
| 5,364,918 A | 11/1994 | Valint et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicolson et al. |
| 5,908,906 A | 6/1999 | Kunzler et al. |
| 5,981,669 A | 11/1999 | Valint et al. |
| 6,087,941 A | 7/2000 | Ferraz et al. |
| 6,131,580 A | 10/2000 | Ratner et al. |
| 6,175,752 B1 | 1/2001 | Say et al. |
| 6,193,369 B1 | 2/2001 | Valint et al. |
| 6,200,626 B1 | 3/2001 | Grobe et al. |
| 6,213,604 B1 | 4/2001 | Valint et al. |
| 6,312,393 B1 | 11/2001 | Abreu |
| 6,348,507 B1 | 2/2002 | Heiler et al. |
| 6,366,794 B1 | 4/2002 | Moussy et al. |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint et al. |
| 6,450,642 B1 | 9/2002 | Jethmalani et al. |
| 6,532,298 B1 | 3/2003 | Cambier et al. |
| 6,550,915 B1 | 4/2003 | Grobe, III |
| 6,570,386 B2 | 5/2003 | Goldstein |
| 6,579,235 B1 | 6/2003 | Abita et al. |
| 6,599,559 B1 | 7/2003 | McGee et al. |
| 6,614,408 B1 | 9/2003 | Mann |
| 6,630,243 B2 | 10/2003 | Valint et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 7,018,040 B2 | 3/2006 | Blum et al. |
| 7,131,945 B2 | 11/2006 | Fink et al. |
| 7,169,106 B2 | 1/2007 | Fleischman et al. |
| 7,398,119 B2 | 7/2008 | Lambert et al. |
| 7,423,801 B2 | 9/2008 | Kaufman et al. |
| 7,429,465 B2 | 9/2008 | Muller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,907,931 B2 | 3/2011 | Hartigan et al. |
| 7,926,940 B2 | 4/2011 | Blum et al. |
| 7,931,832 B2 | 4/2011 | Pugh et al. |
| 7,964,390 B2 | 6/2011 | Rozakis et al. |
| 8,080,187 B2 | 12/2011 | Tepedino, Jr. et al. |
| 8,096,654 B2 | 1/2012 | Amirparviz et al. |
| 8,118,752 B2 | 2/2012 | Hetling et al. |
| 8,142,016 B2 | 3/2012 | Legerton et al. |
| 8,224,415 B2 | 7/2012 | Budiman |
| 8,767,306 B1 | 7/2014 | Miao et al. |
| 8,823,740 B1 | 9/2014 | Amirparviz et al. |
| 2002/0049389 A1 | 4/2002 | Abreu |
| 2002/0193674 A1 | 12/2002 | Fleischman et al. |
| 2003/0179094 A1 | 9/2003 | Abreu |
| 2003/0187338 A1* | 10/2003 | Say ..................... A61M 5/1723 600/345 |
| 2004/0027536 A1 | 2/2004 | Blum et al. |
| 2004/0116794 A1 | 6/2004 | Fink et al. |
| 2005/0016989 A1* | 1/2005 | Kanel ................. H05B 1/0272 219/492 |
| 2005/0045589 A1 | 3/2005 | Rastogi et al. |
| 2005/0221276 A1 | 10/2005 | Rozakis et al. |
| 2006/0072714 A1* | 4/2006 | Sneidern ............. H04M 1/6505 379/88.12 |
| 2007/0016074 A1 | 1/2007 | Abreu |
| 2007/0030443 A1 | 2/2007 | Chapoy et al. |
| 2007/0121065 A1 | 5/2007 | Cox et al. |
| 2007/0188710 A1 | 8/2007 | Hetling et al. |
| 2008/0208335 A1 | 8/2008 | Blum et al. |
| 2008/0218696 A1 | 9/2008 | Mir |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0076367 A1 | 3/2009 | Sit et al. |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2010/0001926 A1 | 1/2010 | Amirparviz et al. |
| 2010/0013114 A1 | 1/2010 | Bowers et al. |
| 2010/0016704 A1 | 1/2010 | Naber et al. |
| 2010/0028559 A1 | 2/2010 | Yan et al. |
| 2010/0072643 A1 | 3/2010 | Pugh et al. |

(56) References Cited

U.S. PATENT DOCUMENTS

| | | |
|---|---|---|
| 2010/0109175 A1 | 5/2010 | Pugh et al. |
| 2010/0110372 A1 | 5/2010 | Pugh et al. |
| 2010/0113901 A1 | 5/2010 | Zhang et al. |
| 2010/0133510 A1 | 6/2010 | Kim et al. |
| 2010/0249548 A1 | 9/2010 | Muller |
| 2011/0015512 A1 | 1/2011 | Pan et al. |
| 2011/0028807 A1 | 2/2011 | Abreu |
| 2011/0040161 A1 | 2/2011 | Abreu |
| 2011/0055317 A1 | 3/2011 | Vonog et al. |
| 2011/0063568 A1 | 3/2011 | Meng et al. |
| 2011/0084834 A1 | 4/2011 | Sabeta |
| 2011/0116035 A1 | 5/2011 | Fritsch et al. |
| 2011/0157541 A1 | 6/2011 | Peyman |
| 2011/0157544 A1 | 6/2011 | Pugh et al. |
| 2011/0184271 A1 | 7/2011 | Veciana et al. |
| 2011/0274680 A1 | 11/2011 | Mazed et al. |
| 2011/0286064 A1 | 11/2011 | Burles et al. |
| 2011/0298794 A1 | 12/2011 | Freedman |
| 2012/0026458 A1 | 2/2012 | Qiu et al. |
| 2012/0038881 A1 | 2/2012 | Amirparviz et al. |
| 2012/0041287 A1 | 2/2012 | Goodall et al. |
| 2012/0041552 A1 | 2/2012 | Chuck et al. |
| 2012/0069254 A1 | 3/2012 | Burton |
| 2012/0075168 A1 | 3/2012 | Osterhout et al. |
| 2012/0075574 A1 | 3/2012 | Pugh et al. |
| 2012/0078071 A1 | 3/2012 | Bohm et al. |
| 2012/0088258 A1 | 4/2012 | Bishop et al. |
| 2012/0092612 A1 | 4/2012 | Binder et al. |
| 2012/0109296 A1 | 5/2012 | Fan |
| 2012/0177576 A1 | 7/2012 | Hu |
| 2012/0201755 A1 | 8/2012 | Rozakis et al. |
| 2012/0245444 A1* | 9/2012 | Otis .................... A61B 5/1486 600/345 |
| 2012/0259188 A1 | 10/2012 | Besling |

FOREIGN PATENT DOCUMENTS

| | | |
|---|---|---|
| EP | 1061874 | 12/2000 |
| EP | 1818008 | 8/2007 |
| EP | 1947501 | 7/2008 |
| EP | 1617757 | 8/2009 |
| WO | 95/04609 | 2/1995 |
| WO | 01/16641 | 3/2001 |
| WO | 01/34312 | 5/2001 |
| WO | 03/065876 | 8/2003 |
| WO | 2004/060431 | 7/2004 |
| WO | 2004/064629 | 8/2004 |
| WO | 2006/015315 | 2/2006 |
| WO | 2009/094643 | 7/2009 |
| WO | 2010/105728 | 9/2010 |
| WO | 2010/133317 | 11/2010 |
| WO | 2011/011344 | 1/2011 |
| WO | 2011/034592 | 3/2011 |
| WO | 2011/035228 | 3/2011 |
| WO | 2011/035262 | 3/2011 |
| WO | 2011/083105 | 7/2011 |
| WO | 2011/163080 | 12/2011 |
| WO | 2012/035429 | 3/2012 |
| WO | 2012/037455 | 3/2012 |
| WO | 2012/051167 | 4/2012 |
| WO | 2012/051223 | 4/2012 |
| WO | 2012052765 | 4/2012 |

OTHER PUBLICATIONS

Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.
Baxter, "Capacitive Sensors," 2000, 17 pages.
Bull, "Different Types of Statistical Analysis," Article Click, Feb. 4, 2008, 4 pages, http://www.articleclick.com/Article/Different-Types-of-Statistical-Analysis/968252, Last accessed Sep. 4, 2012.
Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.
Chu et al., "Biomedical soft contact-lens sensor for in situ ocular biomonitoring of tear contents," Biomed Microdevices, 2011, pp. 603-611, vol. 13.
Chu et al., "Soft contact lens biosensor for in situ monitoring of tear glucose as non-invasive blood sugar assessment," Talanta, 2011, pp. 960-965, vol. 83.
Ho et al., "Contact Lens With Integrated Inorganic Semiconductor Devices," MEMS 2008. IEEE 21st International Conference on. IEEE, 2008., pp. 403-406.
"Integrated circuit," Wikipedia, 9 pages, http://en.wikipedia.org/wiki/Integrated_circuit, Last accessed Sep. 10, 2012.
Lähdesmäki et al., "Possibilities for Continuous Glucose Monitoring by a Functional Contact Lens," IEEE Instrumentation & Measurement Magazine, Jun. 2010, pp. 14-17.
"Linear regression," Wikipedia, 15 pages, http://en.wikipedia.org/wiki/Linear_regression, Last accessed Sep. 10, 2012.
Lingley et al., "A contact lens with integrated micro solar cells," Microsyst Technol, 2012, pp. 453-458, vol. 18.
"Nonlinear regression," Wikipedia, 4 pages, http://en.wikipedia.org/wiki/Nonlinear_regression, Last accessed Sep. 10, 2012.
Parviz, Babak A., "For Your Eyes Only," IEEE Spectrum, Sep. 2009, pp. 36-41.
"Photolithography," Wikipedia, 8 pages, http://en.wikipedia.org/wiki/Photolithography, Last accessed Sep. 10, 2012.
"Polyvinylidene flouride," Wikipedia, 4 pages, http://en.wikipedia.org/wiki/Polyvinylidene_flouride, Last accessed Mar. 30, 2012.
"Regression analysis," Wikipedia, 11 pages, http://en.wikipedia.org/wiki/Regression_analysis, Last accessed Sep. 6, 2012.
Saeedi, E. et al., "Self-assembled crystalline semiconductor optoelectronics on glass and plastic," J. Micromech. Microeng., 2008, pp. 1-7, vol. 18.
Saeedi et al., "Self-Assembled Inorganic Micro-Display on Plastic," Micro Electro Mechanical Systems, 2007. MEMS. IEEE 20th International Conference on. IEEE, 2007., pp. 755-758.
Sensimed Triggerfish, Sensimed Brochure, 2010, 10 pages.
Shih, Yi-Chun et al., "An Inductorless DC-DC Converter for Energy Harvesting With a 1.2-µW Bandgap-Referenced Output Controller," IEEE Transactions on Circuits and Systems-II: Express Briefs, Dec. 2011, pp. 832-836, vol. 58, No. 12.
Shum et al., "Functional modular contact lens," Proc. of SPIE, 2009, pp. 73970K-1 to 73970K-8, vol. 7397.
"Statistics," Wikipedia, 10 pages, http://en.wikipedia.org/wiki/Statistics, Last accessed Sep. 6, 2012.
Stauth et al., "Self-assembled single-crystal silicon circuits on plastic," PNAS, Sep. 19, 2006, pp. 13922-13927, vol. 103, No. 38.
"Understanding pH measurement," Sensorland, 8 pages, http://www.sensorland.com/HowPage037.html, Last accessed Sep. 6, 2012.
Yao, H. et al., "A contact lens with integrated telecommunication circuit and sensors for wireless and continuous tear glucose monitoring," J. Micromech. Microeng., 2012, pp. 1-10, vol. 22.
Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.
Yao et al., "A contact lens with embedded sensor for monitoring tear glucose level," Biosensors and Bioelectronics, 2011, pp. 3290-3296, vol. 26.
Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.
Yeager et al., "A 9 µA, Addressable Gen2 Sensor Tag for Biosignal Acquistion," IEEE Journal of Solid-State Circuits, Oct. 2010, pp. 2198-2209, vol. 45, No. 10.
Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.
Bionic contact lens 'to project emails before eyes,' http://www.kurzweilai.netforums/topic/bionic-contact-lens-to-project-emails-before-eyes, Last accessed Mar. 14, 2012, 2 pages.

(56) References Cited

OTHER PUBLICATIONS

Brahim, et al., "Polypyrrole-hydrogel composites for the construction of clinically important biosensors," 2002, Biosensors & Bioelectronics, pp. 53-59, vol. 17.
Chen, et al., "Microfabricated Implantable Parylene-Based Wireless Passive Intraocular Pressure Sensors," Journal of Microelectromechanical Systems, Dec. 2008, pp. 1342-1351, vol. 17, No. 6.
Chu, et al., "Soft Contact-lens Sensor for Monitoring Tear Sugar as Novel Wearable Device of Body Sensor Network," http://www.ksi.edu/seke/dms11/DMS/2_Kohji_Mitsubayashi.pdf, Last accessed Jul. 27, 2012, 4 pages.
"Contact Lenses: Look Into My Eyes," The Economist, Jun. 2, 2011 , http://www.economist.com/node/18750624/print, Last accessed Mar. 13, 2012, 8 pages.
Haders, "New Controlled Release Technologies Broaden Opportunities for Ophthalmic Therapies," Drug Delivery Technology, Jul./Aug. 2009, pp. 48-53, vol. 8, No. 7.
Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012. 5 pages.
Huang, et al., "Wrinkling of Ultrathin Polymer Films," Mater. Res. Soc. Symp. Proc., 2006, 6 pages, vol. 924, Materials Research Society.
Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.
Liao, et al., "A 3-µW CMOS Glucose Sensor for Wireless Contact-Lens Tear Glucose Monitoring ," IEEE Journal of Solid-State Circuits, Jan. 2012, pp. 335-344, vol. 47, No. 1.
Liao, et al., "A 3-µW Wirelessly Powered CMOS Glucose Sensor for an Active Contact Lens," 2011 IEEE International Solid-State Circuits Conference, Session 2, Feb. 21, 2011, 3 pages.
Lingley, et al., "A Single-Pixel Wireless Contact Lens Display," Journal of Micromechanics and Microengineering, 2011, pp. 1-8.
Lingley, et al., "Multipurpose integrated active contact lenses," SPIE, 2009, 2 pages.
Liu, et al., "Miniature Amperometric Self-Powered Continuous Glucose Sensor with Linear Response," Analytical Chemistry, 2012, 7 pages.
Loncar, et al., "Design and Fabrication of Silicon Photonic Crystal Optical Waveguides," Journal of Lightwave Technology, Oct. 2000, pp. 1402-1411, vol. 18, No. 10.
Murdan, "Electro-responsive drug delivery from hydrogels," Journal of Controlled Release, 2003, pp. 1-17, vol. 92.
Pandey, et al., "A Fully Integrated RF-Powered Contact Lens With a Single Element Display," IEEE Transactions on Biomedical Circuits and Systems, Dec. 2010, pp. 454-461, vol. 4, No. 6.
Parviz, Babak A., "Augmented Reality in a Contact Lens," IEEE Spectrum, Sep. 2009, http://spectrumieee.org/biomedical/bionics/augmented-reality-in-a-contact-lens/0, Last accessed Mar. 14, 2012, 6 pages.
Selner, et al., "Novel Contact Lens Electrode Array for Multi-electrode Electroretinography (meERG)," IEEE, 2011, 2 pages.
Singh , et al., "Novel Approaches in Formulation and Drug Delivery using Contact Lenses," Journal of Basic and Clinical Pharmacy, May 2011, pp. 87-101, vol. 2, Issue 2.
Thomas, et al., "Functional Contact Lenses for Remote Health Monitoring in Developing Countries," IEEE Global Humanitarian Technology Conference, 2011, pp. 212-217, IEEE Computer Society.
Tweedie, et al., "Contact creep compliance of viscoelastic materials via nanoindentation," J. Mater. Res., Jun. 2006, pp. 1576-1589, vol. 21, No. 2, Materials Research Society.
Wall, K., "Active contact lens that lets you see like the Terminator patented," Feb. 10, 2012, http://www.patexia.com/feed/active-contact-lens-that-lets-you-see-like-the-terminator-patented-2407, Last accessed Mar. 28, 2012, 5 pages.
Zarbin, et al., "Nanotechnology in ophthalmology," Can J Ophthalmol, 2010, pp. 457-476, vol. 45, No. 5.

\* cited by examiner

US 9,737,248 B1

CANCELLATION OF A BASELINE CURRENT SIGNAL VIA CURRENT SUBTRACTION WITHIN A LINEAR RELAXATION OSCILLATOR-BASED CURRENT-TO-FREQUENCY CONVERTER CIRCUIT

CROSS-REFERENCE TO RELATED APPLICATION

This application is a continuation of U.S. patent application Ser. No. 13/610,788, filed Sep. 11, 2012, which is incorporated herein by reference.

TECHNICAL FIELD

This disclosure generally relates to systems and/or methods for subtracting in the current domain an output current primary signal from a primary sensor from an output current reference signal from a reference sensor to produce a frequency output signal indicative of the difference between the output current primary signal and the output current reference signal.

BACKGROUND OF THE INVENTION

Electrochemical sensors typically have a baseline output signal that fluctuates over time, temperature, and voltage potential. This baseline signal is generally undesirable since it is often indistinguishable from a signal produced by a parameter being measured by the electrochemical sensor. Conventionally, such baseline signal is removed by employing a reference electrochemical sensor that produces the baseline signal, but does not produce the signal associated with the parameter being measured, in conjunction with a primary electrochemical sensor that produces a total signal comprising the baseline signal and the signal associated with the parameter being measured. The difference between the total signal produced by the primary electrochemical sensor and the signal produced by the reference electrochemical sensor is the signal associated with the measured parameter. Conventionally, electrochemical sensors produce output current signals that are converted to voltage or a digital format for analysis, such as subtracting a primary signal from a reference signal as discussed above. This generally requires the primary electrochemical sensor and the reference electrochemical sensor to each have a separate readout circuit to convert the output current signal. This is not an issue in an environment where power requirements and physical space are not limiting factors, such as a non-portable electrochemical sensing device. However, where power requirements and physical space are limited (e.g., such as with respect to a contact lens), employment of multiple readout circuits can be problematic.

DETAILED DESCRIPTION

Overview

Figure 1A:
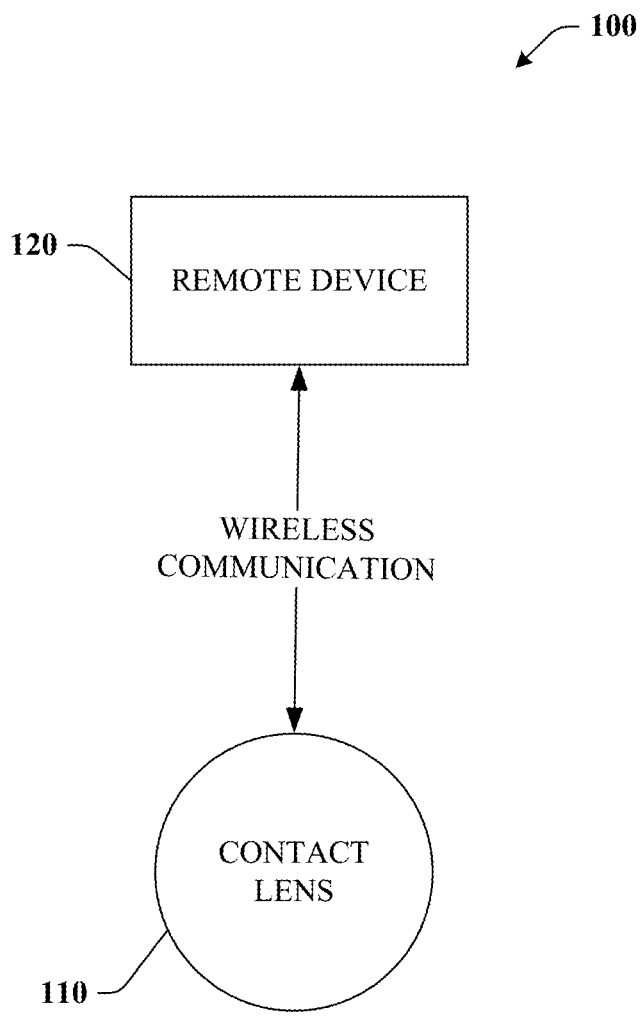
FIG. 1A illustrates a diagram of an exemplary non-limiting system for system for detecting (or inferring) measurement of a parameter associated with a wearer of the contact lens in accordance with an implementation of this disclosure.

Various aspects or features of this disclosure are described with reference to the drawings, wherein like reference numerals are used to refer to like elements throughout. In this specification, numerous specific details are set forth in order to provide a thorough understanding of this disclosure. It should be understood, however, that certain aspects of this disclosure may be practiced without these specific details, or with other methods, components, materials, etc. In other instances, well-known structures and devices are shown in block diagram form to facilitate describing this disclosure.

In accordance with various disclosed aspects, a linear relaxation oscillator-based current-to-frequency converter circuit (hereinafter referred to as "LROCF converter circuit") is provided for subtracting in the current domain an output current primary signal associated with a primary sensor from an output current reference signal associated with a reference sensor to produce a frequency output signal indicative of the difference between the output current primary signal and the output current reference signal.

It is to be appreciated that, while embodiments disclosed herein refer to electrochemical sensors, any suitable sensors that produce an output current signal can be employed. Furthermore, example embodiments herein refer to electrochemical sensors for measuring glucose level. However, sensors for measuring any suitable parameter can be employed, non-limiting examples of which include: temperature, moisture, acidity, or specific minerals, gases, chemicals, biological agents, or proteins, etc. Additionally, example embodiments herein refer to a contact lens, however, any suitable device can employ the linear relaxation oscillator-based current-to-frequency converter circuit, non-limiting examples of which include: a skin patch, a wearable device, a non-wearable device, a portable device, or a non-portable device.

Referring now to the drawings, FIG. 1A depicts a system 100 for detecting (or inferring) measurement of a parameter (e.g., glucose level) associated with a wearer of the contact lens. System 100 includes a contact lens 110 that determines (or infers) information related to measurement of a parameter (hereinafter referred to as "measurement information"), such as glucose level of the wearer of the contact lens. In addition, contact lens 110 can utilize the measurement information locally to control features of contact lens 110 (e.g., issuing commands, adjusting content presentation, activating or deactivating options or components (e.g., high/low glucose warning LED indicators), or any other suitable function). Furthermore, contact lens 110 can optionally communicate measurement information to a remote device 120 for employment in connection with operations associated with the remote device 120 (e.g., analyzing measurement information, adjusting content presentation, activating or deactivating options or components (e.g., a wearable insulin pump), requesting instructions or information, issuing commands, or any other suitable function). Contact lens 110 and remote device 120 can also receive input from users, for example to control interaction with and presentation of content, or operation of contact lens 110 or remote device 120, see e.g., FIG. 5 and corresponding disclosure.

Figure 5:
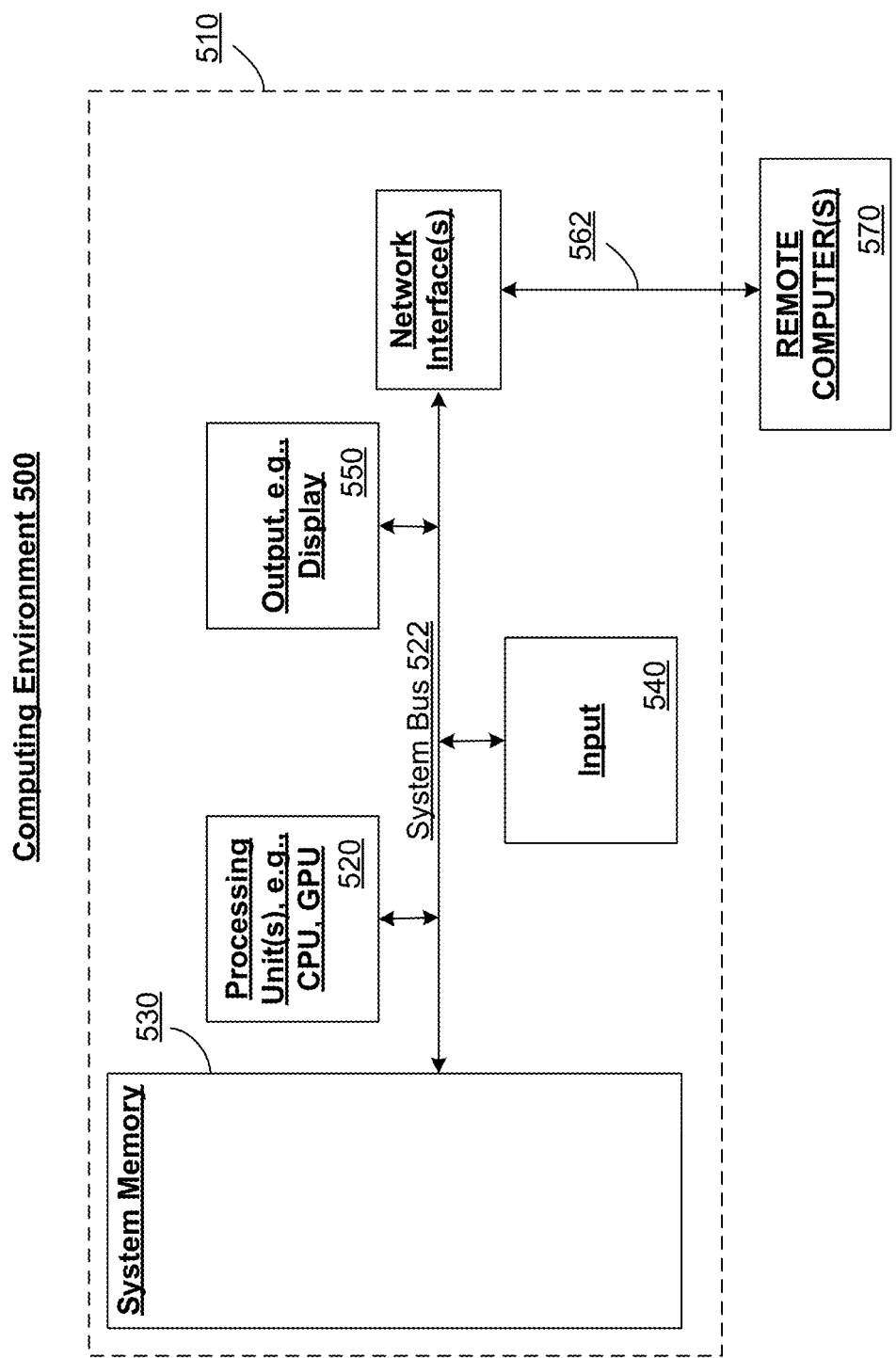
FIG. 5 is a block diagram representing an exemplary non-limiting computing system or operating environment in which the various embodiments can be implemented.

Contact lens 110 and remote device 120, respectively include a memory that stores computer executable components and a processing circuit, which can include a processor, that executes computer executable components stored in the memory (see e.g., FIG. 5). Contact lens 110 and remote device 120 can communicate via a wireless network. It is to be appreciated that while only one remote device 120 is depicted, contact lens 110 can communicate with any suitable number of remote devices 120 concurrently, serially, an ad hoc manner, or in accordance with any suitable protocol. Additionally, remote device 120 can communicate with any suitable number of contact lenses 110 concurrently, serially, an ad hoc manner, or in accordance with any suitable protocol.

Remote device 120, can include a wearable device or a non-wearable device. Wearable device can include, for example, heads-up display glasses, a monocle, eyeglasses, sunglasses, a headset, a visor, a cap, a helmet, a mask, a headband, clothing, or any other suitable device that can be worn by a human or non-human user and can communicate with contact lens 110 remotely. Non-wearable device can include, for example, a mobile device, a mobile phone, a camera, a camcorder, a video camera, personal data assistant, laptop computer, tablet computer, desktop computer, server system, cable set top box, satellite set top box, cable modem, television set, monitor, media extender device, blu-ray device, DVD (digital versatile disc or digital video disc) device, compact disc device, video game system, portable video game console, audio/video receiver, radio device, portable music player, navigation system, car stereo, or any suitable device that can communicate with a contact lens 110 remotely. Moreover, remote device 120 and contact lens 110 can include a display and/or user interface (e.g., a web browser or application), that can generate, receive and/or present graphical indicia (e.g., displays, text, video . . . ) generated locally or remotely.

Figure 1B:
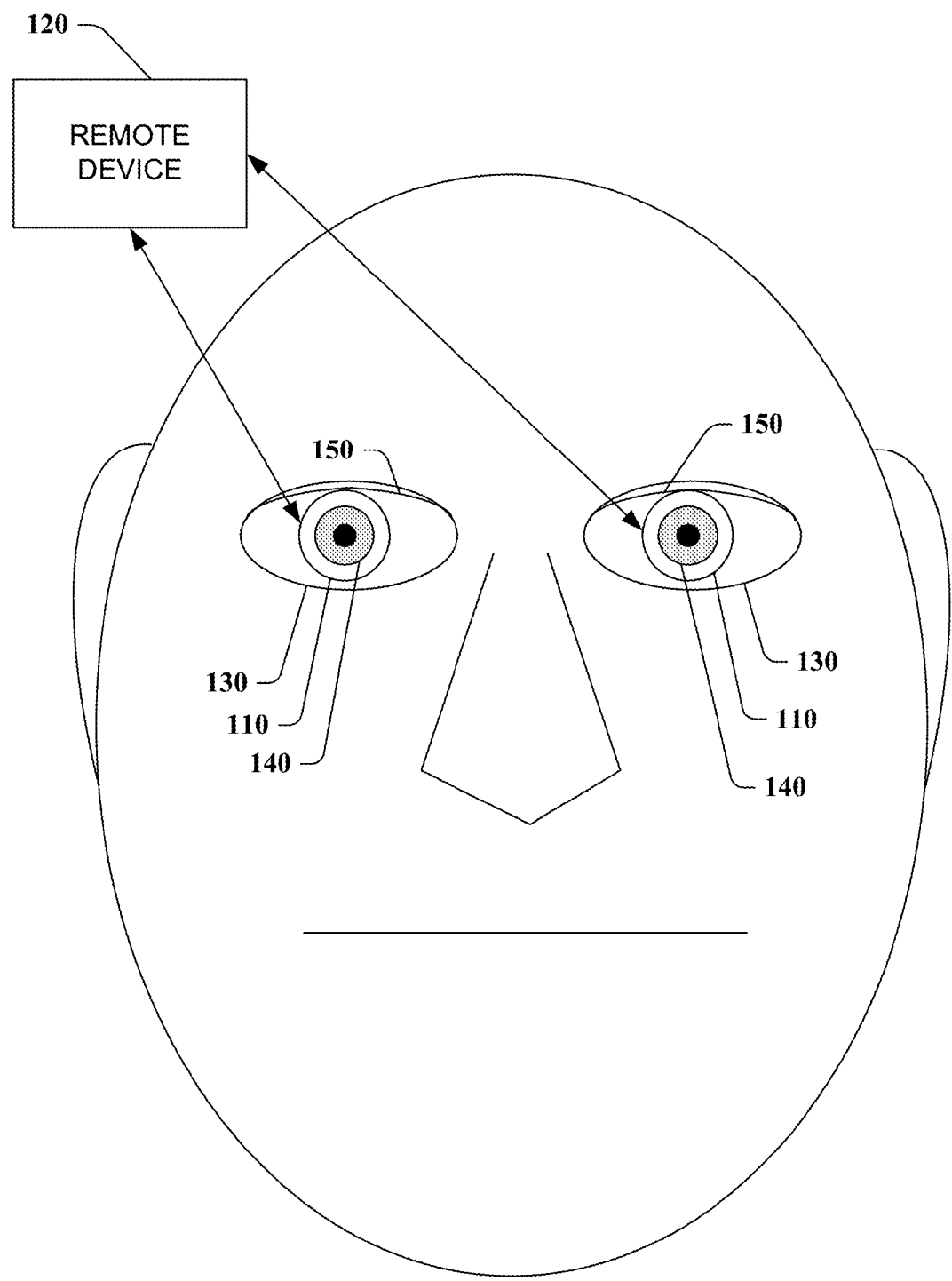
FIG. 1B illustrates a diagram of the exemplary non-limiting system of FIG. 1A worn on both eyes of a human user in accordance with an implementation of this disclosure.

Referring to FIG. 1B, system 100 is depicted on a human user. Contact lenses 110 are shown worn on both eyes 130, covering irises 140 while eyelids 150 are open. Remote device 120 is shown with one or more transceivers (not shown) arranged to communicate wirelessly with contact lenses 110. It is to be further appreciated that respective transceivers of remote device 120 can have transmission power and/or signal reception sensitivity suitable for transmitting a signal to and/or receiving a signal from an associated contact lenses 110 on an eye without interfering with another contact lenses 110 on another eye. While FIG. 1B depicts a contact lenses 110 arrangement in both eyes, it is to be appreciated that an arrangement with a contact lens 110 on one eye can be employed.

Figure 2A:
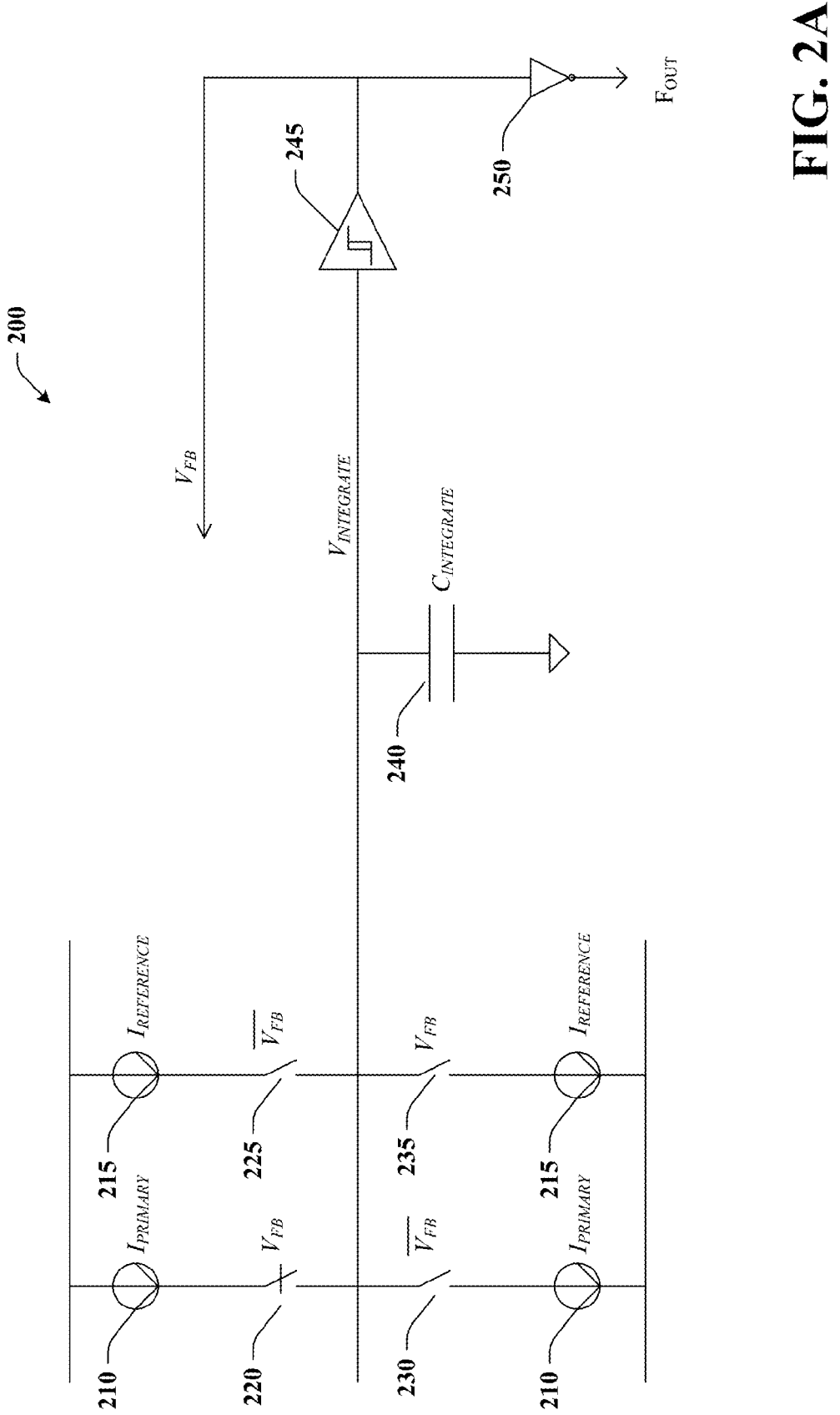
FIG. 2A illustrates a diagram of an exemplary non-limiting linear relaxation oscillator-based current-to-frequency converter circuit accordance with an implementation of this disclosure.

Referring to FIG. 2A, an LROCF converter circuit 200 is depicted for subtracting an output current primary signal $I_{PRIMARY}$ from a primary sensor 210 from an output current reference signal $I_{REFERENCE}$ from a reference sensor 215 in the current domain to produce an output frequency signal $F_{OUT}$ indicative of the difference between $I_{PRIMARY}$ and $I_{REFERENCE}$. Primary sensor 210 is a sensor that produces an output current signal during measurement of a parameter. In an embodiment, primary sensor 210 is an electrochemical sensor for measuring a parameter, such as glucose level in tears produced by eye 130. An enzyme in primary sensor 210 reacts with glucose in the tears to produce a measurement current signal indicative of amount of glucose in the tears. Primary sensor 210 also produces a baseline current signal that fluctuates over time, temperature, and voltage potential. As such, $I_{PRIMARY}$ comprises the baseline current signal and the measurement current signal. Reference sensor 215 can be any suitable sensor that produces a baseline current signal substantially similar to the baseline current signal produced by primary sensor 210, but does not produce the measurement current signal in the presence of the measured parameter (e.g., glucose in the tears). In an embodiment, reference sensor 215 is an electrochemical sensor, but it should be appreciated that reference sensor 215 does not have to be an electrochemical sensor and does not have to match a sensor type of the primary sensor 210. The difference between $I_{PRIMARY}$ and $I_{REFERENCE}$ represents measurement current signal $I_{NET}$ indicative of measurement of the parameter (e.g., amount of glucose in the tears).

LROCF converter circuit 200 includes inverter 250. LROCF converter circuit 200 also includes switches 220, 225, 230, and 235 whose state is based upon feedback voltage $V_{FB}$ derived from a voltage $V_{INTEGRATE}$ on integration capacitor 240 having a capacitance $C_{INTEGRATE}$. LROCF converter circuit 200 further includes amplifier 245 that is employed to generate $V_{FB}$ from $V_{INTEGRATE}$. In an embodiment, amplifier 245 is employed that has hysteresis designed therein, such as a Schmitt trigger. It should be noted that other embodiments can employ an amplifier without hysteresis.

Figure 2B:
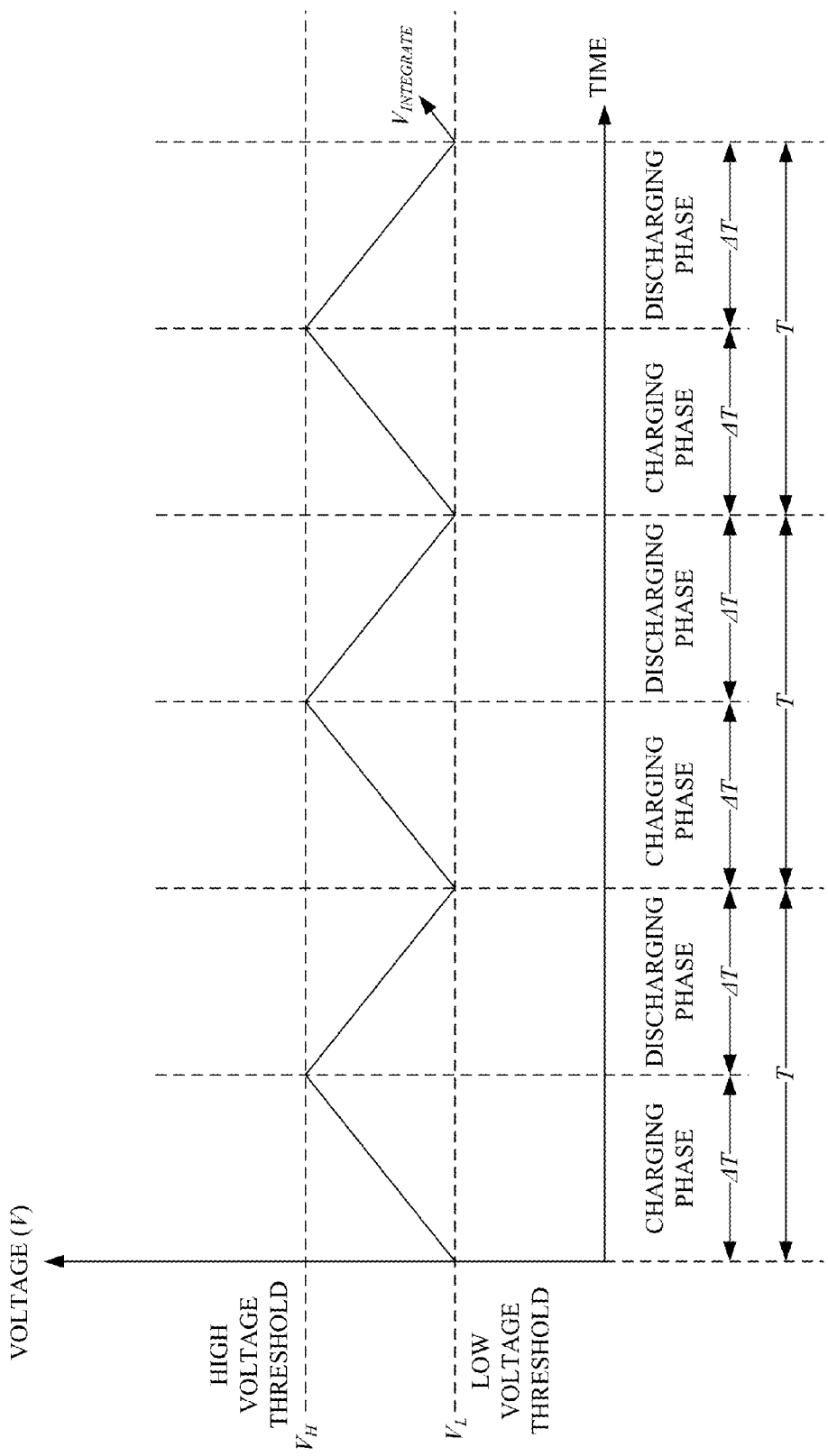
FIG. 2B illustrates a diagram of an exemplary non-limiting chart associated with operation of the linear relaxation oscillator-based current-to-frequency converter circuit with respect to feedback voltage and charging/discharging phases of integration capacitor in accordance with an implementation of this disclosure.

Referring to FIG. 2B, a chart is illustrated that is associated with operation of LROCF converter circuit 200 with respect to $V_{INTEGRATE}$ and charging/discharging phases of integration capacitor 240. As current signals $I_{PRIMARY}$ and $I_{REFERENCE}$ are produced during measurement of the parameter, LROCF converter circuit 200 enters a charging phase where $I_{PRIMARY}$ is pushed into integration capacitor 240 while $I_{REFERENCE}$ is concurrently pulled from integration capacitor 240. This creates voltage $V_{INTEGRATE}$ on integration capacitor 240. When $V_{INTEGRATE}$ reaches a high voltage threshold $V_H$ the state of switches 220, 225, 230, and 235 change in response to $V_{FB}$ such that LROCF converter circuit 200 enters a discharging phase where $I_{PRIMARY}$ is pulled from integration capacitor 240 while $I_{REFERENCE}$ is concurrently pushed onto integration capacitor 240. As a result, voltage $V_{INTEGRATE}$ decreases until reaching a low voltage threshold $V_H$, at which switches 220, 225, 230, and 235 change in response to $V_{FB}$ such that LROCF converter circuit 200 enters the charging phase again. While $I_{PRIMARY}$ and $I_{REFERENCE}$ are produced during measurement of the parameter, LROCF converter circuit 200 continuously alternates between charging and discharging phases which causes the LROCF converter circuit 200 to produce output frequency signal $F_{OUT}$ shown in FIG. 2A. The following equations illustrate the relationship between $F_{OUT}$, $I_{PRIMARY}$ and $I_{REFERENCE}$.

$$I_{NET} = I_{PRIMARY} - I_{REFERENCE} \quad \text{Equation (1)}$$

$$\Delta V = V_H - V_L \quad \text{Equation (2)}$$

$$I_{NET} = C_{INTEGRATE} \frac{\Delta V}{\Delta T} \quad \text{Equation (3)}$$

$$\Delta T = C_{INTEGRATE} \frac{\Delta V}{I_{NET}} \quad \text{Equation (4)}$$

$$T = 2 \frac{C_{INTEGRATE} \Delta V}{I_{NET}}, \quad \text{Equation (5)}$$

where $T$ is the time period of oscillation $$F_{OUT} = \frac{I_{NET}}{2 C_{INTEGRATE} \Delta V} \quad \text{Equation (6)}$$

$$I_{NET} = F_{OUT} 2 C_{INTEGRATE} \Delta V \quad \text{Equation (7)}$$

As such, output frequency signal $F_{OUT}$ is linear with measurement current signal $I_{NET}$. Therefore, the output frequency signal $F_{OUT}$ can be employed given known values of $C_{INTEGRATE}$, $V_H$, and $V_L$ associated with LROCF converter circuit 200 to determine $I_{NET}$, e.g., using equation (7). In an embodiment, the value of $I_{NET}$ can be employed to determine (of infer) a value associated with the measured parameter (e.g. glucose level), for example using a function, lookup table, or any suitable mechanism that relates values of $I_{NET}$ to corresponding values of the measured parameter. In another embodiment, the value of $F_{OUT}$ can be employed to determine (of infer) a value associated with the measured parameter, for example using a function, lookup table, or any suitable mechanism that relates values of $F_{OUT}$ to corresponding values of the measured parameter.

Figure 2C:
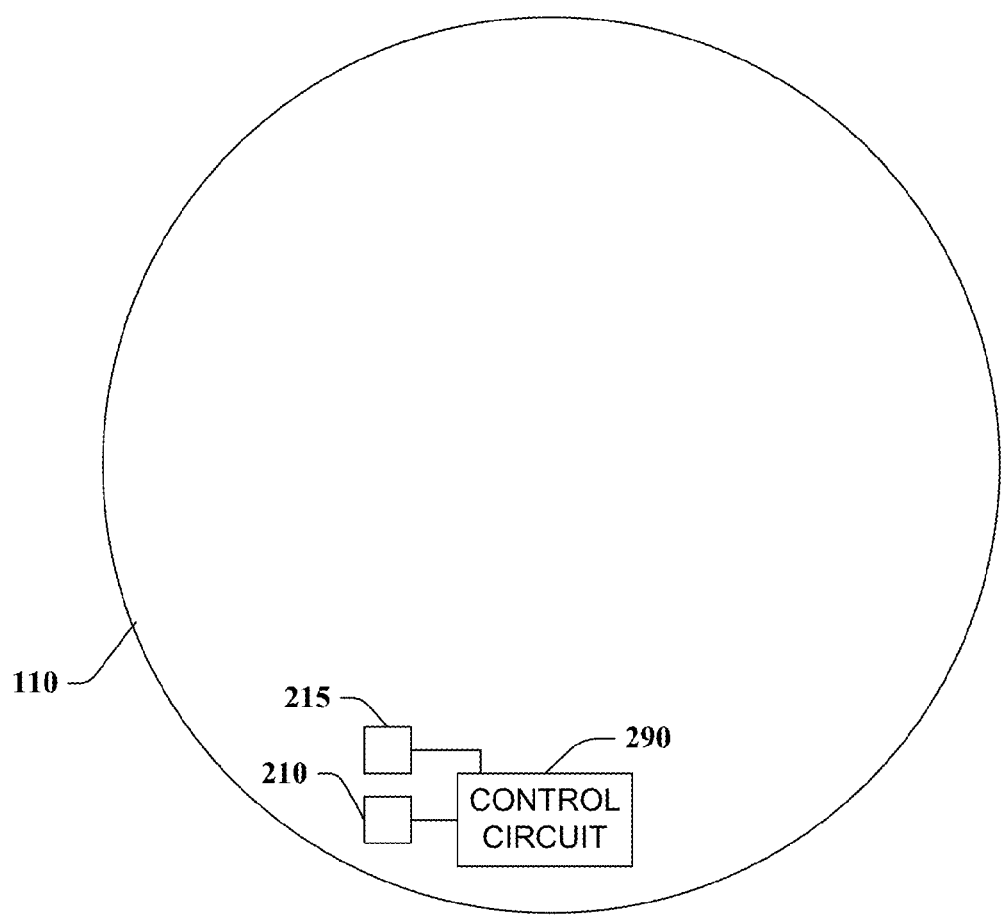
FIG. 2C illustrates a diagram of an exemplary non-limiting contact lens from FIG. 1A in accordance with an implementation of this disclosure.

Referring to FIG. 2C, contact lens 110 is depicted that includes, disposed on or within its substrate, a control circuit 290, primary sensor 210, and reference sensor 215. Control circuit 290 is coupled via wire to primary sensor 210 and reference sensor 215 to receive output current signals. It is to be further appreciated that different aspects of interaction between control circuit 290, and primary sensor 210 and reference sensor 215 may be respectively coupled via wire or wirelessly. In one example, all interactions are coupled via wire. In a further example, some interactions are coupled wirelessly, while other interactions are coupled via wire. For example, communication interaction may be coupled wirelessly, while power supply interactions and current signals may be coupled via wire. It is to be appreciated that primary sensor 210 and reference sensor 215 can respectively be uniquely identifiable to control circuit 290, for example, via an identifier signal or identifying information conveyed respectively from primary sensor 210 and reference sensor 215 to control circuit 290. It is also to be appreciated that control circuit 290, primary sensor 210, and reference sensor 215 can be located at any suitable locations of contact lens 110.

Figure 2D:
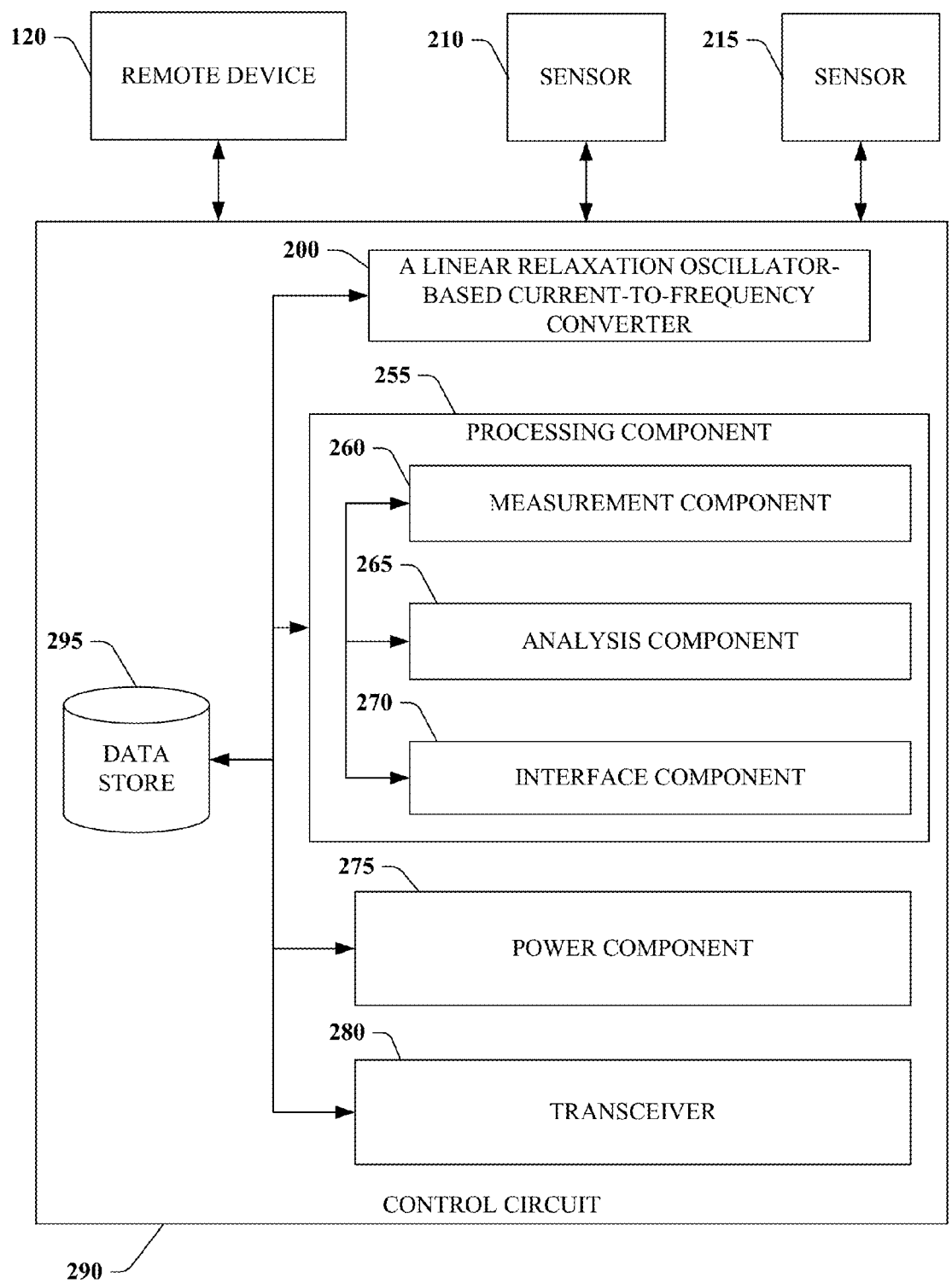
FIG. 2D illustrates a diagram of an exemplary non-limiting control circuit that determines (or infers) measurement information associated with a measured parameter in accordance with an implementation of this disclosure.

Referring to FIG. 2D, is depicted control circuit 290 that includes processing component 255 that determines (or infers) measurement information associated with a measured parameter of primary sensor 210, and communicates with remote device 120, primary sensor 210, and reference sensor 215. Control circuit 290 also includes LROCF converter circuit 200 that converts current signals $I_{PRIMARY}$ and $I_{REFERENCE}$ from primary sensor 210 and reference sensor 215 respectively into an output frequency signal $F_{OUT}$ indicative of the difference between $I_{PRIMARY}$ and $I_{REFERENCE}$ as disclosed above. In addition, control circuit 290 can include power component 275 that manages, receives, generates, stores, and/or distributes usable electrical power to other components of contact lens 110. Control circuit 290 can also include one or more transceivers 280 for transmitting or receiving signals to or from remote device 120, primary sensor 210, or reference sensor 215. It is to be appreciated that primary sensor 210 or reference sensor 215 may interface directly with processing component 255 without need to employ transceiver 280, for example through a wired coupling. Additionally, control circuit 290 can include a data store 295 that can store data from processing component 255, LROCF converter circuit 200, power component 275, transceiver 280, remote device 120, primary sensor 210, or reference sensor 215. Data store 295 can reside on any suitable type of storage device, non-limiting examples of which are illustrated with reference to FIGS. 4 and 5, and corresponding disclosure.

With continued reference to FIG. 2D, processing component 255 includes measurement component 260 that instructs primary sensor 210 or reference sensor 215 to measure a parameter concurrently. It is to be appreciated that one or both of primary sensor 210 or reference sensor 215 can continuously or periodically at predetermined intervals measure the parameter, thereby not requiring instructions from measurement component 260. It is to be appreciated that any suitable interval for measuring the parameter can be employed.

During measurement of the parameter, LROCF converter circuit 200 produces output frequency signal $F_{OUT}$ which is analyzed by analysis component 265 to determine (or infer) measurement information. It is to be appreciated that measurement information can include, a frequency value corresponding to $F_{OUT}$, an amount of current corresponding to $I_{NET}$, a value for the measured parameter based upon $F_{OUT}$ or $I_{NET}$ as discussed above, or any other suitable information related to or derived from measurement of the parameter. It is to be appreciated that analysis component 265 can employ various algorithms and mathematical functions to determine (or infer) measurement information. In an embodiment, analysis component 265 can determine (or infer) measurement information by employing data from $F_{OUT}$ in conjunction with a threshold. It is to be appreciated that a threshold can be any suitable condition, for example, a greater than condition, less than condition, equal to condition, one or more ranges, or function. For example, specific frequency ranges can correspond to specific glucose levels. In addition, analysis component 265 can employ measurement information obtained at multiple points in time to track measurement values of the parameter. For example, glucose level can be tracked by time of day to monitor spikes after meal times. In another example, glucose level can be tracked over several days to determine an average glucose level. In a further example, analysis component 265 can track measurement over a period of time to identify patterns associated with the measured parameter. It is further to be appreciated that analysis of measurement information can be performed by remote device 120.

Continuing with reference to FIG. 2D, interface component 270 can communicate measurement information to remote device 120 using one or more transceivers 280. Furthermore, interface component 270 can receive data or commands from remote device 120 using the one or more transceivers 280. For example, interface component 270 can receive a request for measurement information from remote device 120 and respond to the request with measurement information. In another example, interface component 270, can receive a command from remote device 120 for measurement component 260 to instruct primary sensor 210 or reference sensor 215 to measure a parameter concurrently. In a further example, analysis by remote device 120 of measurement information can indicate a problem and remote device 120 can send a command to interface component 270 for processing component 255 to present a warning indication or message on a display integrated into contact lens 110.

Power component 275 can include any suitable power source that can manage, receive, generate, store, and/or distribute necessary electrical power for the operation of various components of multi-sensor contact lens 110. For example, power component 275 can include but is not limited to a battery, a capacitor, a solar power source, radio frequency power source, electrochemical power source, temperature power source, or mechanically derived power source (e.g., MEMs system). In another example, power component 275 receives or generates usable electrical power from signals from one or more sensors (e.g., photodiode, pressure, heat, conductivity, electric field, magnetic, electrochemical, etc.) integrated into contact lens 110. Transceiver 280 can transmit and receive information to and from, or within contact lens 110. In some embodiments, transceiver 280 can include an RF antenna.

It is to be appreciated that in accordance with one or more implementations described in this disclosure, users can opt-in or opt-out of providing personal information, demographic information, location information, proprietary information, sensitive information, or the like in connection with data gathering aspects. Moreover, one or more implementations described herein can provide for anonymizing collected, received, or transmitted data.

Figure 3:
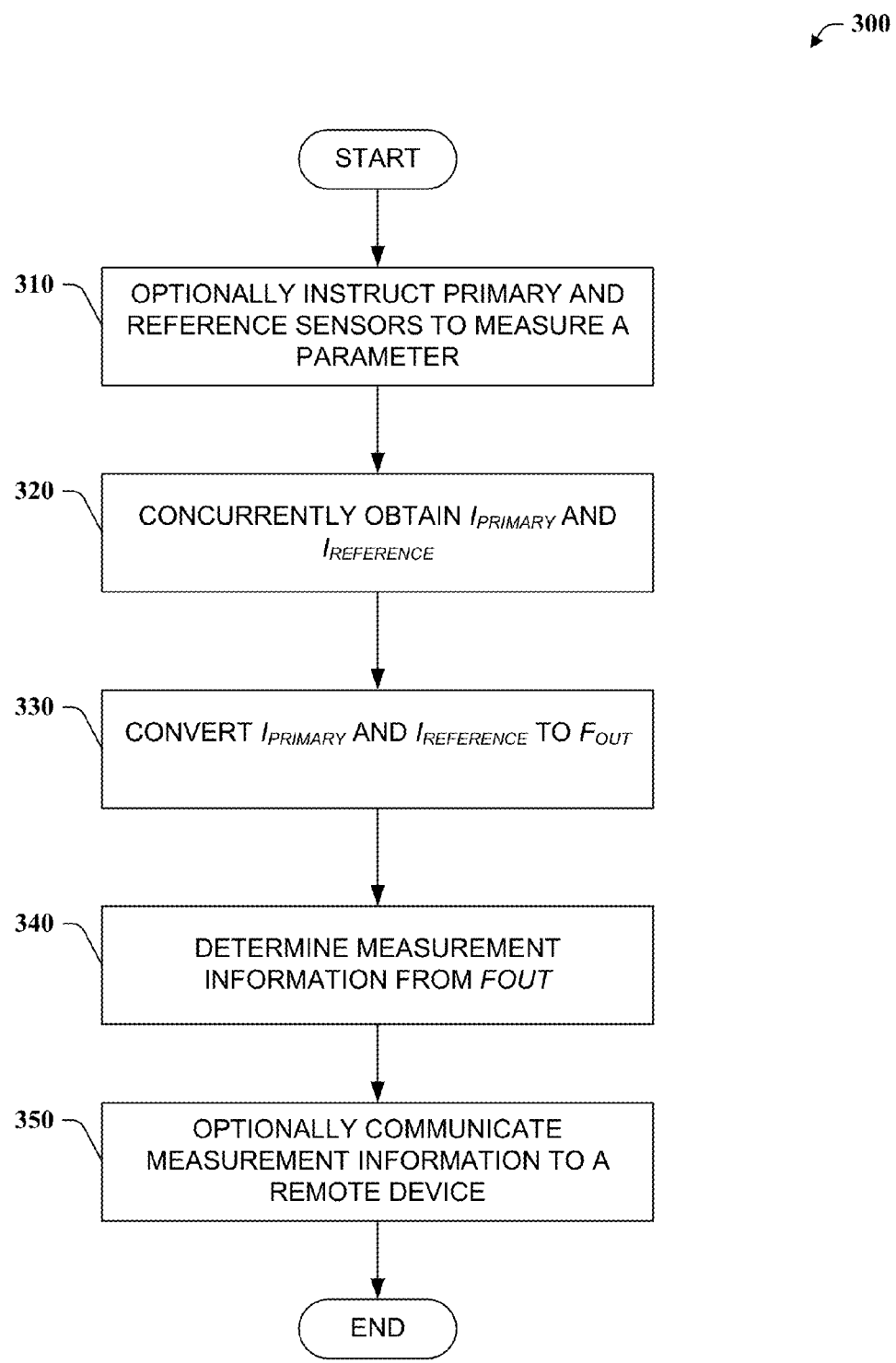
FIG. 3 illustrates an exemplary non-limiting flow diagram for detecting (or inferring) measurement of a parameter in accordance with an implementation of this disclosure.

FIG. 3 illustrates various methodologies in accordance with certain disclosed aspects. While, for purposes of simplicity of explanation, the methodologies are shown and described as a series of acts, it is to be understood and appreciated that the disclosed aspects are not limited by the order of acts, as some acts may occur in different orders and/or concurrently with other acts from that shown and described herein. For example, those skilled in the art will understand and appreciate that a methodology can alternatively be represented as a series of interrelated states or events, such as in a state diagram. Moreover, not all illustrated acts may be required to implement a methodology in accordance with certain disclosed aspects. Additionally, it is to be further appreciated that the methodologies disclosed hereinafter and throughout this disclosure are capable of being stored on an article of manufacture to facilitate transporting and transferring such methodologies to computers.

Referring to FIG. 3, an exemplary method 300 for determining measurement information is depicted. At reference numeral 310, an optional act of instructing a primary sensor and reference sensor to concurrently measure a parameter is performed (e.g. by a measurement component 260 or control circuit 290). As noted above, it is to be appreciated that one or both of the primary sensor or reference sensor can continuously or periodically measure the parameter. At reference numeral 320, current signals $I_{PRIMARY}$ and $I_{REFERENCE}$ from a primary sensor and reference sensor respectively are obtained associated with a measured parameter (e.g. by a measurement component 260, LROCF converter circuit 200, processing component 255, or control circuit 290). At reference numeral 330, $I_{PRIMARY}$ and $I_{REFERENCE}$ are converted into an output frequency signal $F_{OUT}$ indicative of the difference between $I_{PRIMARY}$ and $I_{REFERENCE}$ (e.g. by a LROCF converter circuit 200). At reference numeral 340, measurement information for the measured parameter is determined (or inferred) based on the output frequency signal $F_{OUT}$ (e.g. by an analysis component 265 or control circuit 290). At reference numeral 350, an optional act of communicating measurement information to a remote device and/or receiving information from a remote device is performed (e.g. by an interface component 270 or control circuit 290).

Exemplary Networked and Distributed Environments

One of ordinary skill in the art can appreciate that the various embodiments described herein can be implemented in connection with any computer or other client or server device, which can be deployed as part of a computer network or in a distributed computing environment, and can be connected to any kind of data store where media may be found. In this regard, the various embodiments described herein can be implemented in any computer system or environment having any number of memory or storage units, and any number of applications and processes occurring across any number of storage units. This includes, but is not limited to, an environment with server computers and client computers deployed in a network environment or a distributed computing environment, having remote or local storage.

Distributed computing provides sharing of computer resources and services by communicative exchange among computing devices and systems. These resources and services include the exchange of information, cache storage and disk storage for objects, such as files. These resources and services can also include the sharing of processing power across multiple processing units for load balancing, expansion of resources, specialization of processing, and the like. Distributed computing takes advantage of network connectivity, allowing clients to leverage their collective power to benefit the entire enterprise. In this regard, a variety of devices may have applications, objects or resources that may participate in the various embodiments of this disclosure.

Figure 4:
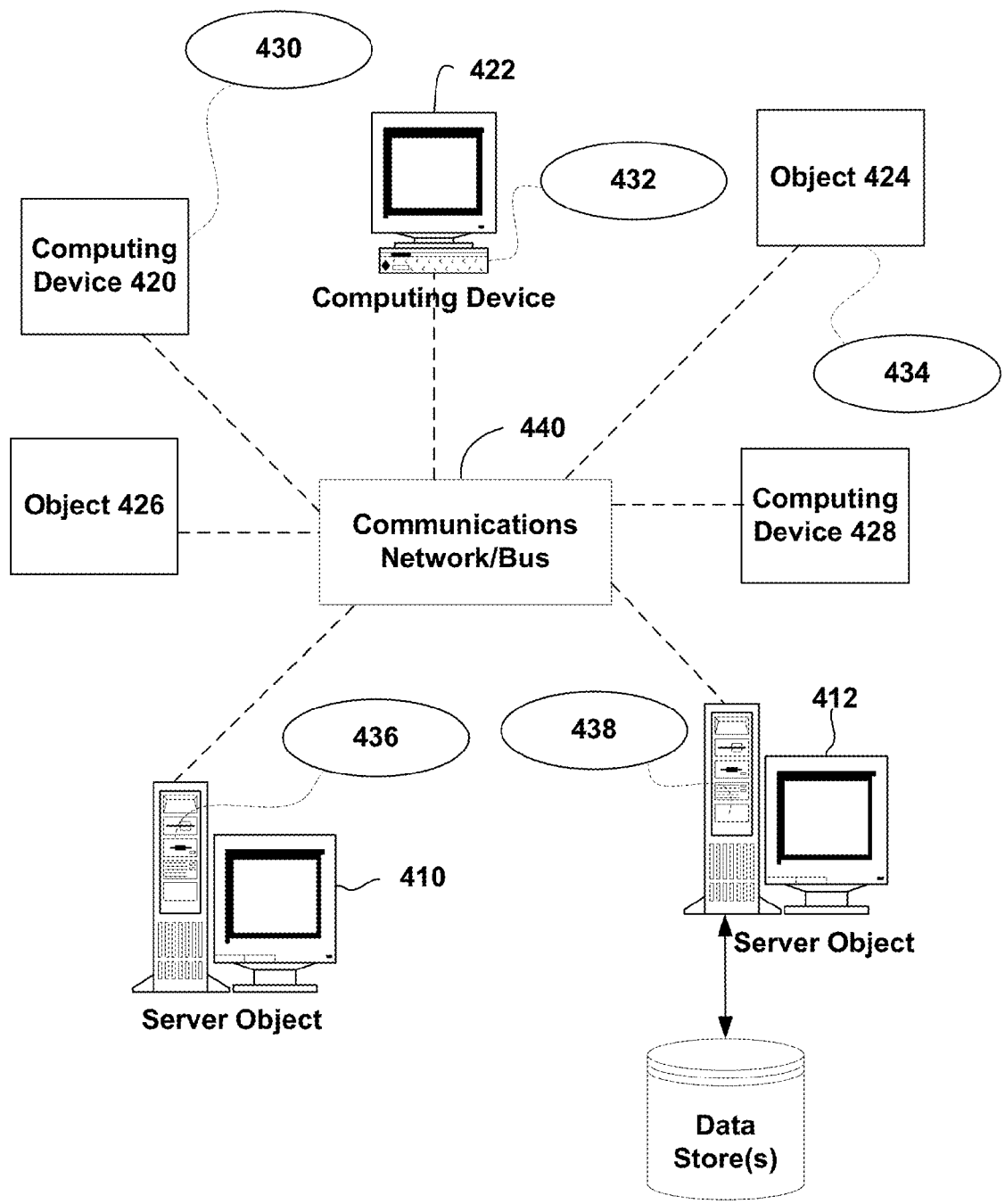
FIG. 4 is a block diagram representing an exemplary non-limiting networked environment in which the various embodiments can be implemented.

FIG. 4 provides a schematic diagram of an exemplary networked or distributed computing environment. The distributed computing environment comprises computing objects 410, 412, etc. and computing objects or devices 420, 422, 424, 426, 428, etc., which may include programs, methods, data stores, programmable logic, etc., as represented by applications 430, 432, 434, 436, 438. It can be appreciated that computing objects 410, 412, etc. and computing objects or devices 420, 422, 424, 426, 428, etc. may comprise different devices, such as personal digital assistants (PDAs), audio/video devices, mobile phones, MP3 players, personal computers, laptops, tablets, etc.

Each computing object 410, 412, etc. and computing objects or devices 420, 422, 424, 426, 428, etc. can communicate with one or more other computing objects 410, 412, etc. and computing objects or devices 420, 422, 424, 426, 428, etc. by way of the communications network 440, either directly or indirectly. Even though illustrated as a single element in FIG. 4, network 440 may comprise other computing objects and computing devices that provide services to the system of FIG. 4, and/or may represent multiple interconnected networks, which are not shown. Each computing object 410, 412, etc. or computing objects or devices 420, 422, 424, 426, 428, etc. can also contain an application, such as applications 430, 432, 434, 436, 438, that might make use of an API, or other object, software, firmware and/or hardware, suitable for communication with or implementation of various embodiments of this disclosure.

There are a variety of systems, components, and network configurations that support distributed computing environments. For example, computing systems can be connected together by wired or wireless systems, by local networks or widely distributed networks. Currently, many networks are coupled to the Internet, which provides an infrastructure for widely distributed computing and encompasses many different networks, though any suitable network infrastructure can be used for exemplary communications made incident to the systems as described in various embodiments herein.

Thus, a host of network topologies and network infrastructures, such as client/server, peer-to-peer, or hybrid architectures, can be utilized. The "client" is a member of a class or group that uses the services of another class or group. A client can be a computer process, e.g., roughly a set of instructions or tasks, that requests a service provided by another program or process. A client process may utilize the requested service without having to "know" all working details about the other program or the service itself.

In a client/server architecture, particularly a networked system, a client can be a computer that accesses shared network resources provided by another computer, e.g., a server. In the illustration of FIG. 4, as a non-limiting example, computing objects or devices 420, 422, 424, 426, 428, etc. can be thought of as clients and computing objects 410, 412, etc. can be thought of as servers where computing objects 410, 412, etc. provide data services, such as receiving data from client computing objects or devices 420, 422, 424, 426, 428, etc., storing of data, processing of data, transmitting data to client computing objects or devices 420, 422, 424, 426, 428, etc., although any computer can be considered a client, a server, or both, depending on the circumstances. Any of these computing devices may be processing data, or requesting transaction services or tasks that may implicate the techniques for systems as described herein for one or more embodiments.

A server is typically a remote computer system accessible over a remote or local network, such as the Internet or wireless network infrastructures. The client process may be active in a first computer system, and the server process may be active in a second computer system, communicating with one another over a communications medium, thus providing distributed functionality and allowing multiple clients to take advantage of the information-gathering capabilities of the server. Any software objects utilized pursuant to the techniques described herein can be provided standalone, or distributed across multiple computing devices or objects.

In a network environment in which the communications network/bus 440 is the Internet, for example, the computing objects 410, 412, etc. can be Web servers, file servers, media servers, etc. with which the client computing objects or devices 420, 422, 424, 426, 428, etc. communicate via any of a number of known protocols, such as the hypertext transfer protocol (HTTP). Objects 410, 412, etc. may also serve as client computing objects or devices 420, 422, 424, 426, 428, etc., as may be characteristic of a distributed computing environment.

Exemplary Computing Device

As mentioned, advantageously, the techniques described herein can be applied to any suitable device. It is to be understood, therefore, that handheld, portable and other computing devices and computing objects of all kinds are contemplated for use in connection with the various embodiments. Accordingly, the computer described below in FIG. 5 is but one example of a computing device that can be employed with implementing one or more of the systems or methods shown and described in connection with FIGS. 1-5. Additionally, a suitable server can include one or more aspects of the below computer, such as a media server or other media management server components.

Although not required, embodiments can partly be implemented via an operating system, for use by a developer of services for a device or object, and/or included within application software that operates to perform one or more functional aspects of the various embodiments described herein. Software may be described in the general context of computer executable instructions, such as program modules, being executed by one or more computers, such as client workstations, servers or other devices. Those skilled in the art will appreciate that computer systems have a variety of configurations and protocols that can be used to communicate data, and thus, no particular configuration or protocol is to be considered limiting.

FIG. 5 thus illustrates an example of a suitable computing system environment 500 in which one or aspects of the embodiments described herein can be implemented, although as made clear above, the computing system environment 500 is only one example of a suitable computing environment and is not intended to suggest any limitation as to scope of use or functionality. Neither is the computing environment 500 be interpreted as having any dependency or requirement relating to any one or combination of components illustrated in the exemplary operating environment 500.

With reference to FIG. 5, an exemplary computing device for implementing one or more embodiments in the form of a computer 510 is depicted. Components of computer 510 may include, but are not limited to, a processing unit 520, a system memory 530, and a system bus 522 that couples various system components including the system memory to the processing unit 520.

Computer 510 typically includes a variety of computer readable media and can be any available media that can be accessed by computer 510. The system memory 530 may include computer storage media in the form of volatile and/or nonvolatile memory such as read only memory (ROM) and/or random access memory (RAM). By way of example, and not limitation, system memory 530 may also include an operating system, application programs, other program modules, and program data.

A user can enter commands and information into the computer 510 through input devices 540, non-limiting examples of which can include a keyboard, keypad, a pointing device, a mouse, stylus, touchpad, touchscreen, trackball, motion detector, camera, microphone, joystick, game pad, scanner, or any other device that allows the user to interact with computer 510. A monitor or other type of display device is also connected to the system bus 522 via an interface, such as output interface 550. In addition to a monitor, computers can also include other peripheral output devices such as speakers and a printer, which may be connected through output interface 550.

The computer 510 may operate in a networked or distributed environment using logical connections to one or more other remote computers, such as remote computer 570. The remote computer 570 may be a personal computer, a server, a router, a network PC, a peer device or other common network node, or any other remote media consumption or transmission device, and may include any or all of the elements described above relative to the computer 510. The logical connections depicted in FIG. 5 include a network 562, such local area network (LAN) or a wide area network (WAN), but may also include other networks/buses e.g., cellular networks.

As mentioned above, while exemplary embodiments have been described in connection with various computing devices and network architectures, the underlying concepts may be applied to any network system and any computing device or system in which it is desirable to publish or consume media in a flexible way.

Also, there are multiple ways to implement the same or similar functionality, e.g., an appropriate API, tool kit, driver code, operating system, control, standalone or downloadable software object, etc. which enables applications and services to take advantage of the techniques described herein. Thus, embodiments herein are contemplated from the standpoint of an API (or other software object), as well as from a software or hardware object that implements one or more aspects described herein. Thus, various embodiments described herein can have aspects that are wholly in hardware, partly in hardware and partly in software, as well as in software.

The word "exemplary" is used herein to mean serving as an example, instance, or illustration. For the avoidance of doubt, the aspects disclosed herein are not limited by such examples. In addition, any aspect or design described herein as "exemplary" is not necessarily to be construed as preferred or advantageous over other aspects or designs, nor is it meant to preclude equivalent exemplary structures and techniques known to those of ordinary skill in the art. Furthermore, to the extent that the terms "includes," "has," "contains," and other similar words are used in either the detailed description or the claims, for the avoidance of doubt, such terms are intended to be inclusive in a manner similar to the term "comprising" as an open transition word without precluding any additional or other elements.

Computing devices typically include a variety of media, which can include computer-readable storage media and/or communications media, in which these two terms are used herein differently from one another as follows. Computer-readable storage media can be any available storage media that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

On the other hand, communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

As mentioned, the various techniques described herein may be implemented in connection with hardware or software or, where appropriate, with a combination of both. As used herein, the terms "component," "system" and the like are likewise intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on computer and the computer can be a component. One or more components may reside within a process and/or thread of execution and a component may be localized on one computer and/or distributed between two or more computers. Further, a "device" can come in the form of specially designed hardware; generalized hardware made specialized by the execution of software thereon that enables the hardware to perform specific function (e.g., coding and/or decoding); software stored on a computer readable medium; or a combination thereof.

The aforementioned systems have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it is to be noted that one or more components may be combined into a single component providing aggregate functionality or divided into several separate sub-components, and that any one or more middle layers, such as a management layer, may be provided to communicatively couple to such sub-components in order to provide integrated functionality. Any components described herein may also interact with one or more other components not specifically described herein but generally known by those of skill in the art.

In order to provide for or aid in the numerous inferences described herein (e.g. inferring relationships between metadata or inferring topics of interest to users), components described herein can examine the entirety or a subset of the data to which it is granted access and can provide for reasoning about or infer states of the system, environment, etc. from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data.

Such inference can result in the construction of new events or actions from a set of observed events and/or stored event data, whether or not the events are correlated in close temporal proximity, and whether the events and data come from one or several event and data sources. Various classification (explicitly and/or implicitly trained) schemes and/or systems (e.g., support vector machines, neural networks, expert systems, Bayesian belief networks, fuzzy logic, data fusion engines, etc.) can be employed in connection with performing automatic and/or inferred action in connection with the claimed subject matter.

A classifier can map an input attribute vector, x=(x1, x2, x3, x4, xn), to a confidence that the input belongs to a class, as by f(x)=confidence(class). Such classification can employ a probabilistic and/or statistical-based analysis (e.g., factoring into the analysis utilities and costs) to prognose or infer an action that a user desires to be automatically performed. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

In view of the exemplary systems described above, methodologies that may be implemented in accordance with the described subject matter will be better appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Where non-sequential, or branched, flow is illustrated via flowchart, it can be appreciated that various other branches, flow paths, and orders of the blocks, may be implemented which achieve the same or a similar result. Moreover, not all illustrated blocks may be required to implement the methodologies described hereinafter.

In addition to the various embodiments described herein, it is to be understood that other similar embodiments can be used or modifications and additions can be made to the described embodiment(s) for performing the same or equivalent function of the corresponding embodiment(s) without deviating there from. Still further, multiple processing chips or multiple devices can share the performance of one or more functions described herein, and similarly, storage can be effected across a plurality of devices. Accordingly, the invention is not to be limited to any single embodiment, but rather can be construed in breadth, spirit and scope in accordance with the appended claims.

What is claimed is:

1. An eye-mountable device comprising:
a first sensor that produces a first current signal during measurement of at least one parameter, wherein the first current signal comprises a measurement current signal associated with the at least one parameter and a baseline current signal;
a second sensor that produces a second current signal during the measurement of the at least one parameter, wherein the second current signal comprises the baseline current signal and does not include the measurement current signal associated with the at least one parameter; and
a linear relaxation oscillator-based current-to-frequency converter comprising an integration capacitor and a plurality of switches, wherein the integration capacitor has a first terminal connected to the first and second sensors via the plurality of switches and has a second terminal connected to ground, wherein the linear relaxation oscillator-based current-to-frequency converter produces an output frequency signal having a frequency related to a net current corresponding to a difference between the first current signal and the second current signal, wherein the output frequency signal comprises alternating charging phases and discharging phases, wherein during the charging phases the switches connect the first terminal of the integration capacitor to the first and second sensors such that the net current flows into the integration capacitor, and wherein during the discharging phases the switches connect the first terminal of the integration capacitor to the first and second sensors such that the net current flows out from the integration capacitor.

2. The eye-mountable device of claim 1, wherein the first sensor is an electrochemical sensor.

3. The eye-mountable device of claim 2, wherein the second sensor is an electrochemical sensor.

4. The eye-mountable device of claim 1, wherein the baseline current signal varies over at least one of time, temperature, or voltage potential during measurement of the at least one parameter.

5. The eye-mountable device of claim 1, further comprising a processor programmed to analyze the output frequency signal to determine a glucose level.

6. The eye-mountable device of claim 1, further comprising a power component, wherein the power component includes at least one of a battery, a capacitor, a solar power source, a radio frequency power source, an electrochemical power source, a temperature power source, or a mechanically derived power source.

7. The eye-mountable device of claim 1, further comprising a transceiver and an antenna.

8. The eye-mountable device of claim 1, wherein the switches are controlled by a feedback voltage derived from a voltage on the integration capacitor.

9. The eye-mountable device of claim 8, wherein the linear relaxation oscillator-based current-to-frequency converter further comprises an amplifier that generates the feedback voltage from the voltage on the integration capacitor.

10. The eye-mountable device of claim 9, wherein the amplifier is a Schmitt trigger.

11. The eye-mountable device of claim 1, wherein the plurality of switches include a first switch configured to connect a current output of the first sensor to the integration capacitor, a second switch configured to connect a current output of the second sensor to the integration capacitor, a third switch configured to connect a current input of the first sensor to the integration capacitor, and a fourth switch configured to connect a current input of the second sensor to the integration capacitor.

12. The eye-mountable device of claim 11, wherein during the charging phases the first and fourth switches are closed and the second and third switches are open, and wherein during the discharging phases the second and third switches are closed and the first and fourth switches are open.

* * * * *